US007185827B2

(12) United States Patent
Quintard et al.

(10) Patent No.: US 7,185,827 B2
(45) Date of Patent: Mar. 6, 2007

(54) DISPENSING CONTAINER

(75) Inventors: Daniel Quintard, Marly le Roi (FR);
Jacques Lalanne, Compiegne (FR);
Bernard Guglielmini, Crimolois (FR)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 11/217,933

(22) Filed: Sep. 1, 2005

(65) Prior Publication Data
US 2006/0000921 A1    Jan. 5, 2006

Related U.S. Application Data

(63) Continuation of application No. PCT/US04/06747, filed on Mar. 5, 2004.

(60) Provisional application No. 60/455,931, filed on Mar. 19, 2003.

(51) Int. Cl.
*A24F 25/00* (2006.01)

(52) U.S. Cl. .................... 239/55; 239/57; 239/51.5; 239/47; 220/521

(58) Field of Classification Search ............ 239/45, 239/47, 55, 57, 51.5; 220/521, 522, 523; 215/228, 354
See application file for complete search history.

(56) References Cited

U.S. PATENT DOCUMENTS

| 2,456,244 | A | * | 12/1948 | Bash | 239/49 |
| 2,631,890 | A | * | 3/1953 | Fink | 239/47 |
| 2,807,901 | A | | 10/1957 | Gilowitz | |
| 3,035,730 | A | * | 5/1962 | Walker et al. | 215/228 |
| 4,063,665 | A | * | 12/1977 | Schneider et al. | 222/129 |
| 4,732,321 | A | * | 3/1988 | Dolan | 239/45 |
| 4,928,881 | A | * | 5/1990 | Barlics et al. | 239/44 |
| 5,353,546 | A | | 10/1994 | Bock | |
| 5,725,152 | A | * | 3/1998 | Akyu | 239/45 |

* cited by examiner

*Primary Examiner*—Dinh Q. Nguyen
(74) *Attorney, Agent, or Firm*—Ellen K. Park

(57) ABSTRACT

The fragrance emitting dispensing container consists of a container body and a container closure. The container body can be of any shape but preferably is of a decorative shape. The closure functions to close the container and to distribute the fragrance to the room or other space in which the container is present. The closure has a cavity that contains a fragrance emitting material which can be a sheet material or a particulate material. The top of the cavity is a lid with apertures to emit the fragrance into a room. The apertures are covered with a seal which can be partially or fully removed to open the apertures. The seal can be a single seal or a multi-segment seal, with each segment separably removeable to expose a given number of apertures.

17 Claims, 5 Drawing Sheets

DISPENSING CONTAINER

This application is a continuation of application PCT/US2004/06747, filed Mar. 5, 2004, which claims the benefit of U.S. Provisional Application 60/455,931 filed Mar. 19, 2003, both of which are incorporated herein by reference in their entirety.

This invention relates to a fragrance emitting dispensing container. More particularly this invention relates to a dispensing container for a product having a closure that emits a fragrance to impart that fragrance to a room or other space.

BACKGROUND OF THE INVENTION

Many containers for products are used in rooms for which a separate deodorizing fragrance is used. These containers since they are used throughout a day usually are left out on the countertop or similar area. In this way the container can be used to dispense a product into a room.

BRIEF DESCRIPTION OF THE INVENTION

This invention is directed to a fragrance emitting dispensing container. The dispensing container is comprised of the container and a container closure. The container closure contains a fragrance emitting material in a fragrance emitting space within said closure. A removable lid seal closes the fragrance emitting space. The closure is removeably attached to the container and has a projection or similarly functioning means to seal a recess opening in a upper portion of the container for dispensing the product in the container. The removable lid seal is supported by a lid that optionally is removable. The fragrance emitting material that is in the fragrance emitting space can be in any shape or form, and preferably is in a sheet-like form in one or more sections or is in the form of a plurality of particles. The sheet material and particles are of a material that contains the fragrance.

The lid seal can be in a single piece or a plurality of pieces. The lid has a plurality of apertures to allow the fragrance within the closure to be emitted from the closure. The lid seal when in one piece will expose all apertures when removed, and when in more than one section can be removed to open less than all of the apertures and thereby control the release of the fragrance.

The container and the closure can be of a decorative shape with the container and the closure coordinating in the decorative shape. This can be in the shape of a flower, animal, structure or other item that fits the decor of the room in which it is to be used.

The container and closure can be made from essentially any material. These include glass and plastics. The fragrance emitting material can be a plastic or an inorganic substance that has the fragrance adsorbed therein. Such inorganic substances include silicas, aluminas and aluminosilicates such as zeolites.

BRIEF DESCRIPTION OF THE INVENTION

DETAILED DESCRIPTION OF THE INVENTION

Figure 1:
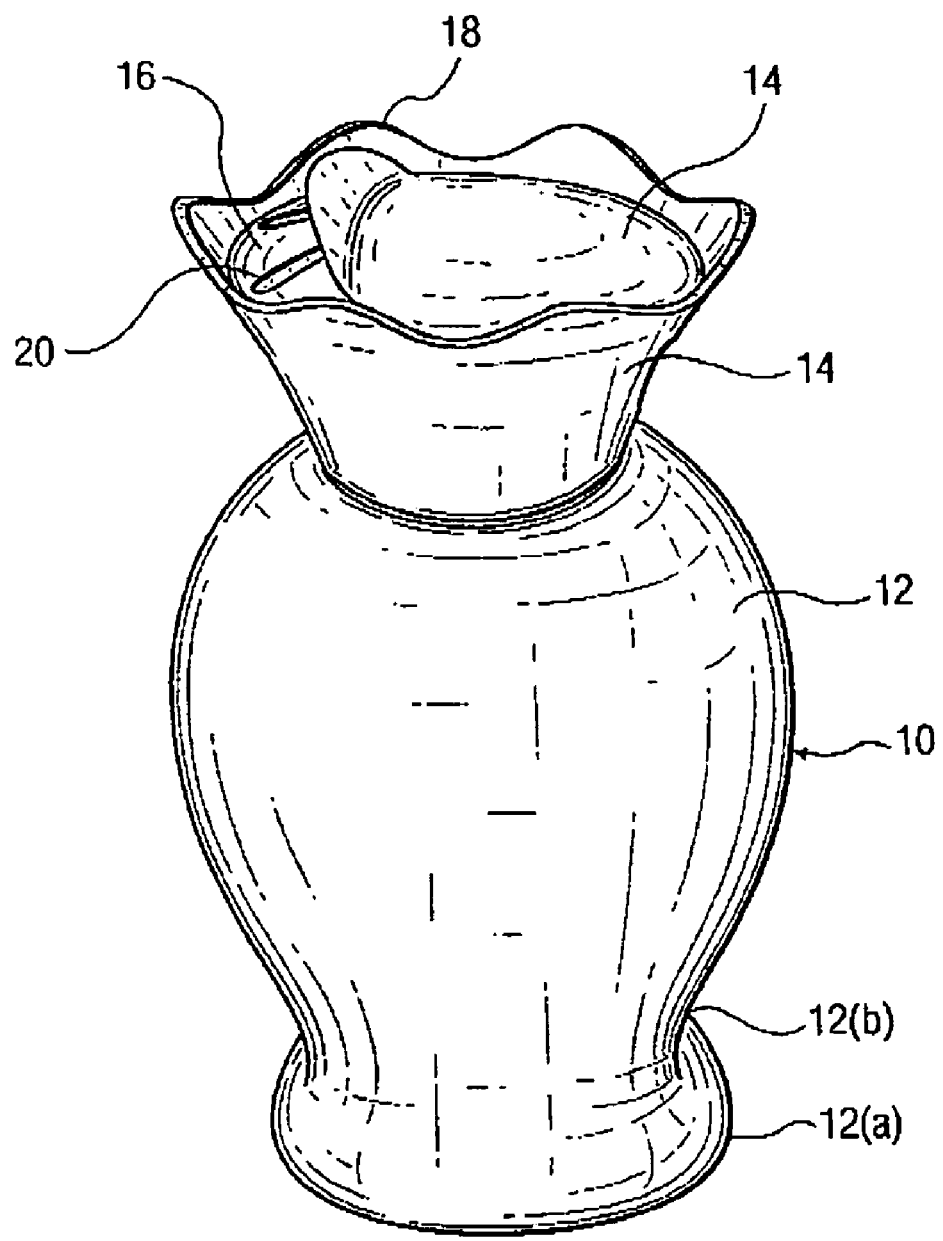
FIG. 1 is a perspective view of the fragrance emitting dispensing container.

The invention will be disclosed in its preferred embodiments with reference to the views in the drawings.

FIG. 1 shows the fragrance emitting dispenser 10 in a perspective view. The fragrance emitting dispensing container 10 is comprised of container 12 and closure 14. The container 12 is a decorative container of a vase-like shape having a base 12(a) and a necked in portion 12(b) adjacent the base. The closure 14 is a decorative closure with flower-like petals 18. The closure has a lid 16 which has a plurality of apertures 20. A removable lid seal 15 closes the aperture prior to the emitting of the fragrance.

Figure 2:
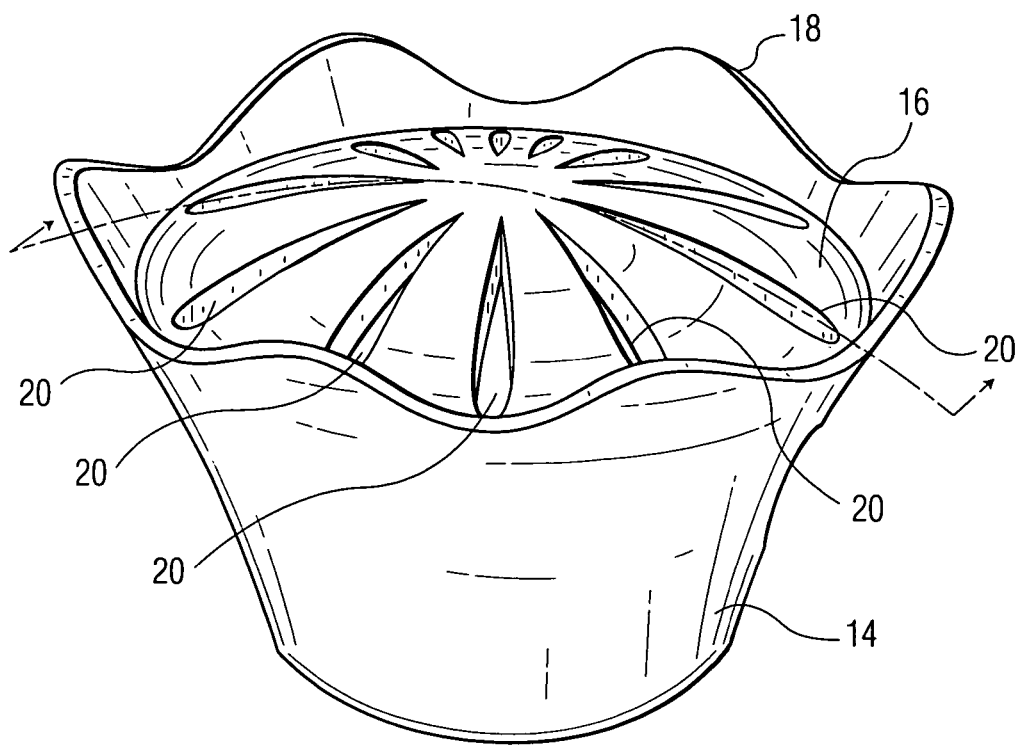
FIG. 2 is a perspective view of the dispensing container closure.
Figure 5:
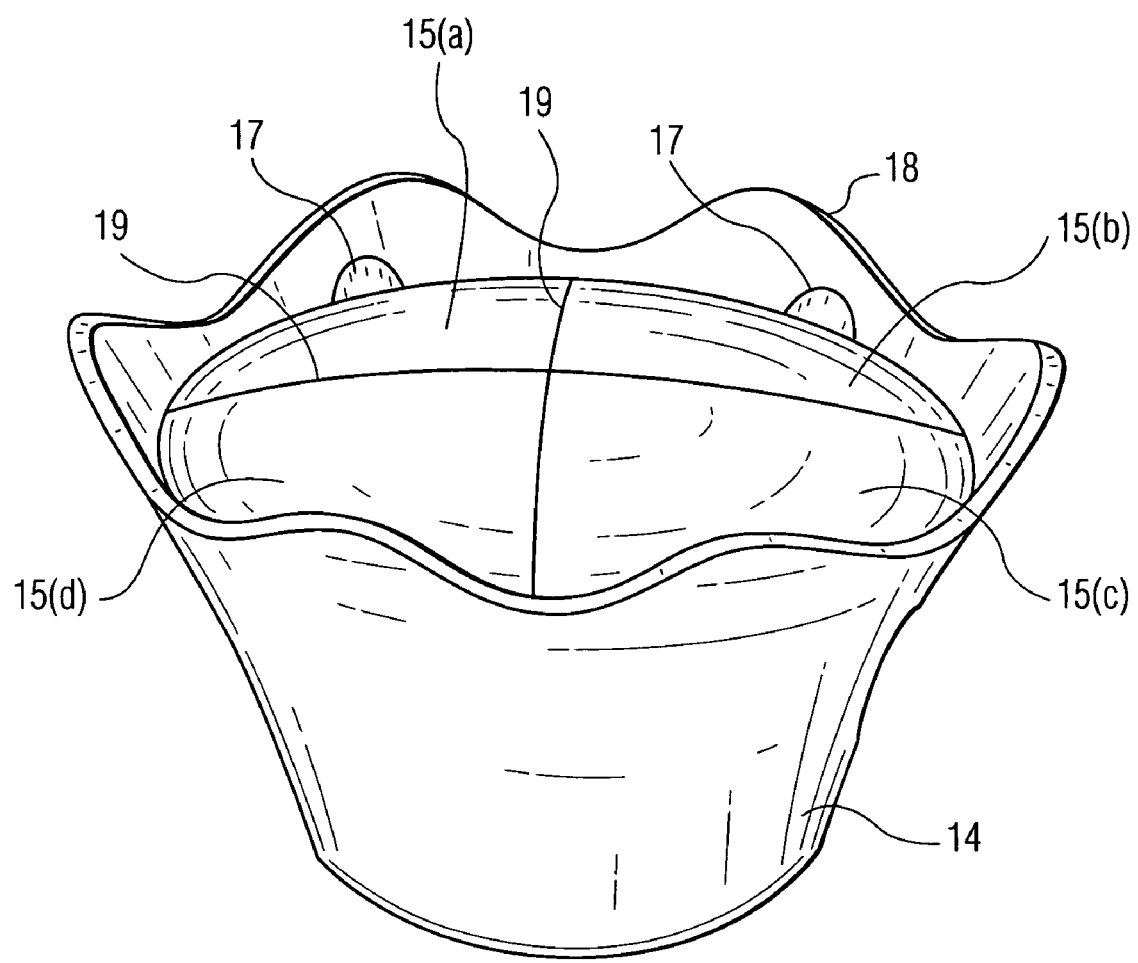
FIG. 5 is a perspective view of the closure showing a sectioned seal.

FIG. 2 is a perspective view of the closure showing the flower-like petals 18 and the apertures 20 in more detail. A plurality of apertures are shown each being designated by 20. The lid seal 15 is removed in this view to show all of the apertures 20 in lid 16. The lid seal can be a single seal as in FIG. 1 which opens all of the apertures or a multiple part seal which opens some of the apertures. This is shown in FIG. 5 along with tabs 17 to grip sections 15(a), 15(b), 15(c) and 15(d). This seal usually will be adhesively attached to the lid. Perforations 19 will separate the sections of the seal.

Figure 3A:
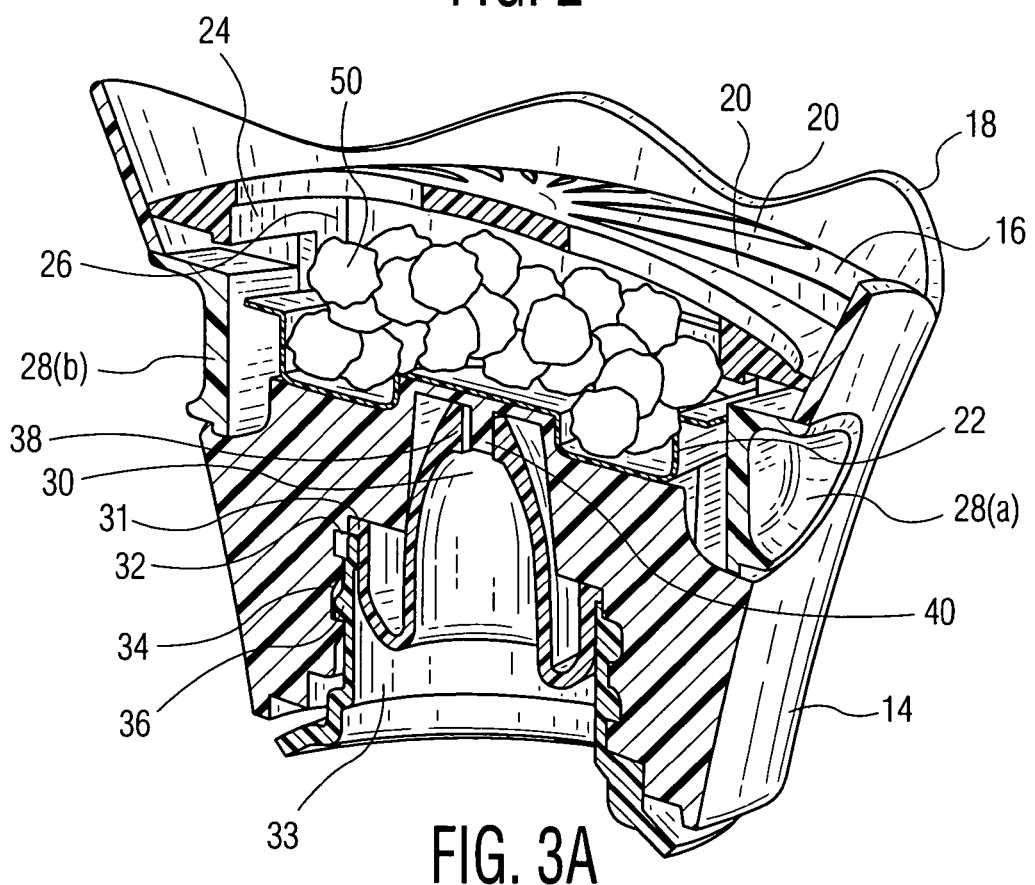
FIG. 3A is a vertical cross-section of the closure of FIG. 2 showing fragranced particles therein.
Figure 3B:
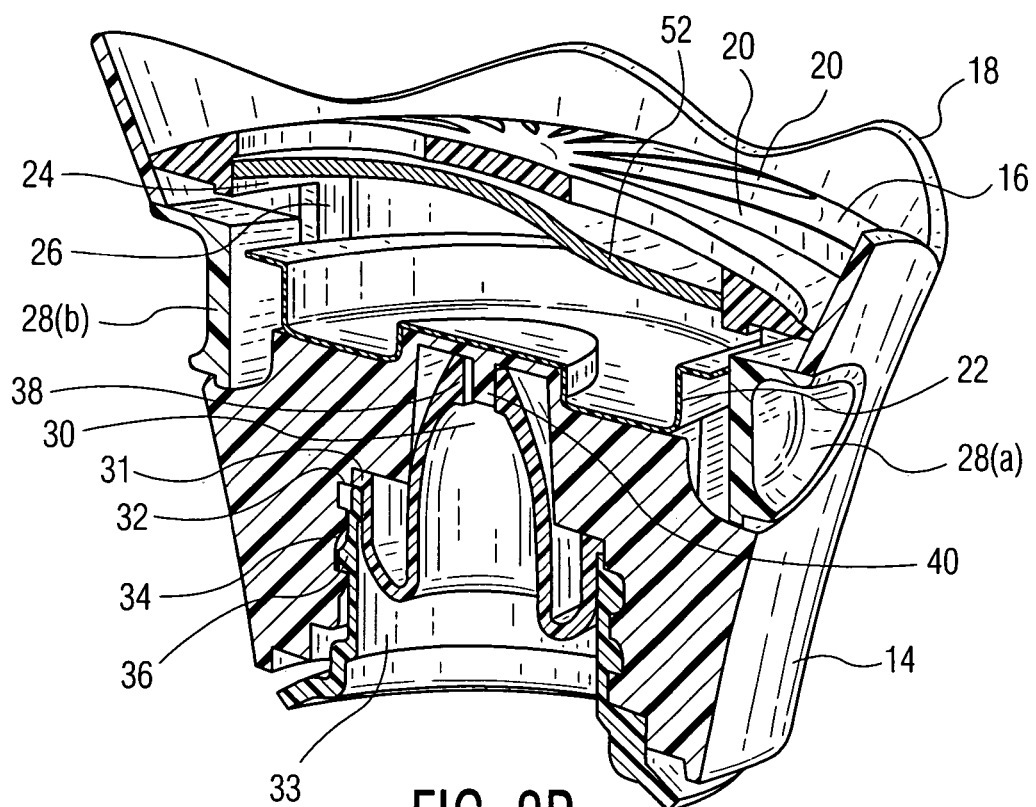
FIG. 3B is a vertical cross-section of the closure of FIG. 2 showing a contained fragranced sheet of material therein.

FIG. 3A shows the closure 14 in more detail in vertical cross-section with fragrance containing particles. FIG. 3B shows a variation of the closure 14 with a fragrance containing sheet; and FIG. 3C the closure 14 without any fragrance material. In FIG. 3A there is shown a plurality of fragrance particles 50 in fragrance emitting space 26. This space is formed by a bottom pan 22, wall 24 and lid 16. The apertures 20 are shown in this view as all being open. The lid seal 15 has been removed. The closure attaches to the container 12 by means of threads 36 on container upper part 33 and threads 34 on the closure. The spout 30 of the container has a dispensing aperture 38 which is closed by projection 40 on the closure. The spout 30 is a friction fit in the container upper part. Also shown is the view are prongs 28(a) and 28(b) which hold the lid 16 onto the closure 14.

Figure 3C:
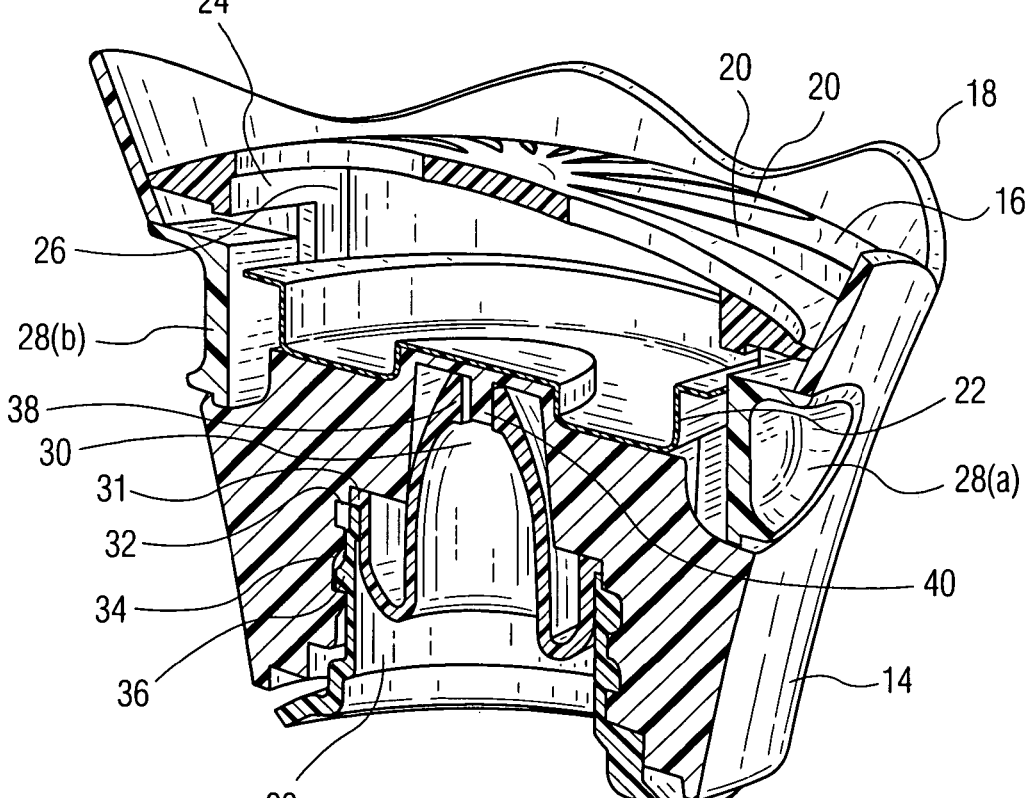
FIG. 3C is a vertical cross section of the closure of FIG. 2 showing the space for the fragrance emitting material.

The closure of FIG. 3B is the same as that of FIG. 3A except that in place of fragranced particles 50 there is a fragranced sheet of material 52 in the fragrance emitting space 26. However, there can be fragrance particles 50 in addition to the sheet of material 52 in fragrance emitting space 26. In FIG. 3C the closure 14 is shown without any fragrance emitting materials.

Figure 4:
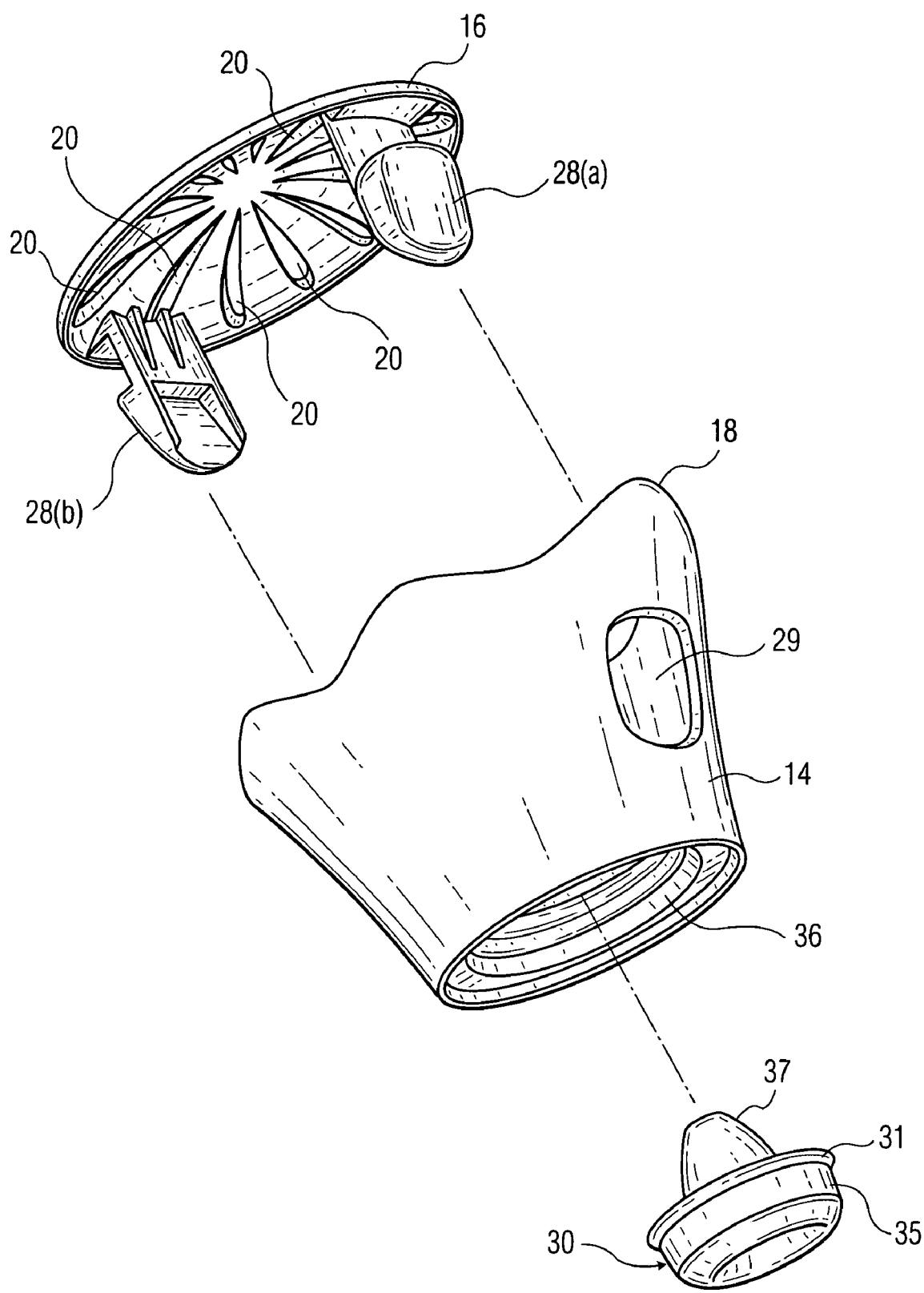
FIG. 4 is an exploded view of the closure of FIG. 2 also showing the container spout.

FIG. 4 shows the closure and spout in an exploded view. This view shows the prongs 28(a) and 28(b) of the lid that interfit into apertures 29(a) and 29(b) (not shown) of the closure. By depressing these prongs they can be released form apertures 29(a) and 29(b) (not shown) and the lid 16 removed from the closure 14. In this way the fragrance emitting material 50,52 can be added to or replaced. In this way when the bottle is refilled with product the fragrance can be refilled. However, fragrance can also be added without refilling the bottle. This is useful if the container is to have a long use life.

The container spout 30 is also shown in more detail in this view. This consists of a nozzle portion 37, flange 31 and wall 35 which is a friction fit into the container. The closure 14 closes the opening in nozzle 37.

The container is easily used for its two purposes. In order to dispense the detergent product in the container the closure is rotated in the manner of any cap closure and removed from the container. The detergent product then is dispensed in the usual way through the spout. After use the closure can be put onto the container by rotating the closure in the direction opposite to that when the closure was removed from the container. The dispensing of the fragrance will occur both when the closure is on the container and when it is off the container. This is controlled through the removal of the seal covering the fragrance emitting apertures. The amount of fragrance emitted can be controlled by the full or partial removal of the seal.

The container can be of any material including glass, but plastics are preferred, and in particular thermoplastics that can be blowmolded. These include the polyolefins and polyesters such as polyethylene terephthalate. The closure can be can be made from any injection moldable plastics, with polyolefins being preferred. The container spout also will be injection molded.

The fragrance emitting material is a material that contains the fragrance. The fragrance is within the material by absorption, adsorption or by being trapped. Suitable fragrances within a plastic are available from International Flavors and Fragrances under the POLYIFF trademark which are ethylene vinyl alcohol or polyethylene plastics which contain and emit a fragrance. Also suitable are fragrances adsorbed onto inorganic materials such as silicas, aluminas and alummosicates such as zeolites.

The present fragrance emitting dispensing container has been described in its preferred embodiments. However, the scope of the invention is described by the concepts which embody the preferred embodiments.

The invention claimed is:

1. A fragrance emitting dispensing container comprising a container and a closure containing a fragrance emitting material, the container having a base at one end and a spout at another end and containing a product to be dispensed from the container through the spout upon removal of the closure from the container, the closure closing said container and the fragrance emitting material located within a fragrance emitting space in said closure, the fragrance emitting space solely within said closure, said closure being removably attached to an upper portion of said container, and at least on one aperture in said fragrance emitting space.

2. A fragrance emitting dispensing container as in claim 1 wherein a lid closes said fragrance emitting space and there is at least one aperture in said lid.

3. A fragrance emitting dispensing container as in claim 1 wherein said lid has a plurality of apertures and a removable lid seal, the removable lid seal covers at least some of said apertures.

4. A fragrance emitting dispensing container as in claim 3 wherein the removable lid seal covers all of said apertures.

5. A fragrance emitting dispensing container as in claim 1 wherein the fragrance emitting material is at least a sheet of material containing a fragrance.

6. A fragrance emitting dispensing container as in claim 1 wherein said fragrance emitting material is a plurality of particles containing a fragrance.

7. A fragrance emitting dispensing container as in claim 1 wherein said closure has a projection which inherits into a recess in the upper portion of said container to close said container.

8. A fragrance emitting dispensing container as in claim 1 wherein said closure is threadedly attached to said upper portion of said container to close said container.

9. A fragrance emitting dispensing container as in claim 8 wherein said closure has a projection which interfits into a recess in said spout to close said container.

10. A fragrance emitting dispensing container as in claim 2 wherein said lid is removeable from said closure whereby said fragrance emitting material may be at least partially replaced with new fragrance emitting material.

11. A fragrance emitting dispensing container as in claim 3 wherein said removable lid seal is in a plurality of sections, each separably removeable from the lid.

12. A fragrance emitting dispensing container as in claim 1 wherein said dispensing container has a decorative shape.

13. A fragrance emitting dispensing container as in claim 12 wherein said closure coordinates with the decorative shape of said dispensing container.

14. A fragrance emitting dispensing container as in claim 1 wherein the dispensing container contains a detergent product which is dispensed from the container through the spout.

15. A fragrance emitting dispensing container as in claim 1 wherein the container is a blow molded polyolefin container.

16. A fragrance emitting dispensing container as in claim 1 wherein the container is a blow molded polyester container.

17. A fragrance emitting dispensing container as in claim 1 wherein the dispensing container is a blow molded polyethylene terephthalate container.

* * * * *